United States Patent
Duran et al.

(10) Patent No.: US 6,352,708 B1
(45) Date of Patent: Mar. 5, 2002

(54) SOLUTION AND METHOD FOR TREATING AUTOLOGOUS TISSUE FOR IMPLANT OPERATION

(75) Inventors: Carlos M. G. Duran, Missoula, MT (US); David T. Cheung, Arcadia; David C. Pang, West Covina, both of CA (US)

(73) Assignee: The International Heart Institute of Montana Foundation, Missoula, MT (US)

( * ) Notice: Subject to any disclaimer, the term of this patent is extended or adjusted under 35 U.S.C. 154(b) by 0 days.

(21) Appl. No.: 09/418,674

(22) Filed: Oct. 14, 1999

(51) Int. Cl.$^7$ .................................................. A61F 2/02
(52) U.S. Cl. ..................... 424/423; 523/113; 523/116
(58) Field of Search .................... 424/423; 523/113, 523/116; 514/772.3

(56) References Cited

U.S. PATENT DOCUMENTS

| | | |
|---|---|---|
| 2,106,261 A | 1/1938 | Weidemann |
| 2,610,625 A | 9/1952 | Sifferd et al. |
| 2,645,618 A | 7/1953 | Ferrari, Jr. |
| 2,659,986 A | 11/1953 | Hink, Jr. |
| 3,939,260 A | 2/1976 | Lafon |
| 4,277,238 A | 7/1981 | Katagiri |
| 4,280,954 A | 7/1981 | Yannas et al. |
| 4,300,243 A | 11/1981 | Baumgartner |
| 4,323,358 A | 4/1982 | Lentz et al. ................. 8/94.11 |
| 4,329,492 A | 5/1982 | Andoh et al. |
| 4,357,274 A | 11/1982 | Werner |
| 4,383,832 A | 5/1983 | Fraefel et al. |
| 4,578,067 A | 3/1986 | Cruz, Jr. |
| 4,703,108 A | 10/1987 | Silver et al. |
| 4,704,131 A | 11/1987 | Noishiki et al. |
| 4,760,131 A | 7/1988 | Sundsmo et al. |
| 4,801,299 A | 1/1989 | Brendel et al. |
| 4,911,915 A | 3/1990 | Fredenburgh |
| 5,028,597 A | 7/1991 | Kodama et al. |
| 5,116,552 A | 5/1992 | Morita et al. |

(List continued on next page.)

FOREIGN PATENT DOCUMENTS

| | | |
|---|---|---|
| GB | 0716161 | 9/1954 |
| WO | 97/32472 | 9/1997 |
| WO | 98/07452 | 2/1998 |
| WO | 99/66967 | 12/1999 |

OTHER PUBLICATIONS

Chachques et al., Ann. NY Acad. Sci. 1988, 529:184.
Love et al., J. Heart Valve Dis. 1992: 1:232–41.
Chauvaud et al., J. Thorac Cardiovasc. Surg. 1991, 102:171–8.
Duran et al., J. Thorac Cardiovasc. Surg. 1995, 11–551–6.
Vyavahare et al., "Ethanol and Aluminum Chloride Pre–incubation to Prevent Bioprosthetic Heart Valve Calcification", Edited by Gabbay & Wheatley, Ch. 14, pp. 173–185, May, 1997.
Rutter et al., Plastic & Reconstructive Surgery, 101(1): 142–6, Jan., 1998.
Vetter et al., Thorac Cardiovasc. Surg., 35(1):11–5, Feb. 1987.

*Primary Examiner*—Carlos Azpuru
(74) *Attorney, Agent, or Firm*—Klein & Szekeres, LLP

(57) ABSTRACT

An aqueous solution containing a water miscible organic solvent, polyethylene glycol and heparine, is used to modify the tissue reactivity of an autologous tissue freshly obtained from a host mammal and to render the tissue temporarily more rigid than in its native state, and better suited for shaping, molding, handling and cutting prior to implantation into the host patient. The implant is highly resistant or immune to thickening, contraction and reduced fibrin deposition after it is implanted and exposed to the bloodstream of the host.

25 Claims, 8 Drawing Sheets

U.S. PATENT DOCUMENTS

| | | |
|---|---|---|
| 5,131,850 A | 7/1992 | Brockbank |
| 5,276,006 A | 1/1994 | Shin et al. |
| 5,296,514 A | 3/1994 | Wang ........................ 424/422 |
| 5,336,616 A | 8/1994 | Livesey et al. |
| 5,476,517 A | 12/1995 | Seifter et al. |
| 5,518,878 A | 5/1996 | Wilkins et al. ............... 435/1.3 |
| 5,558,875 A | 9/1996 | Muller ....................... 514/724 |
| 5,674,290 A | 10/1997 | Li |
| 5,931,969 A | 8/1999 | Carpentier et al. ........... 8/94.11 |
| 5,863,984 A | * 10/1999 | Doillon et al. ............. 525/54.1 |

* cited by examiner

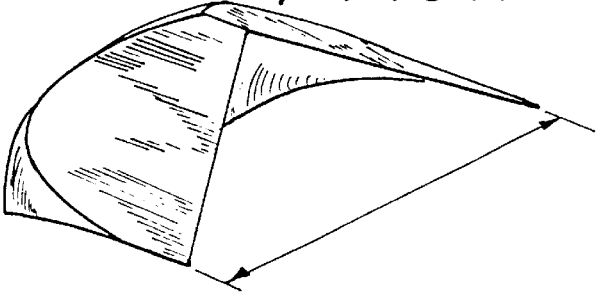
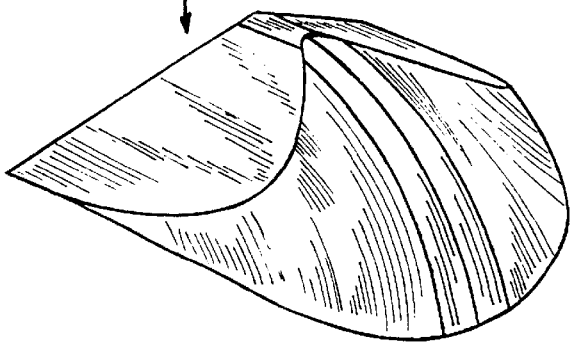
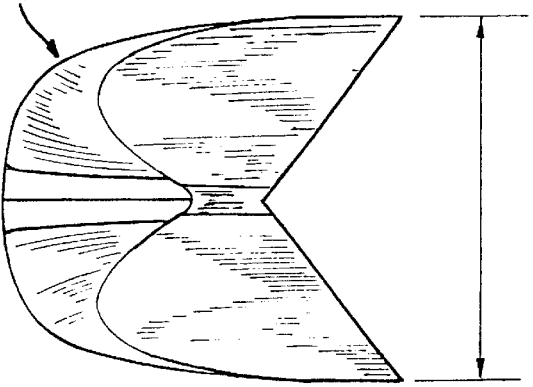
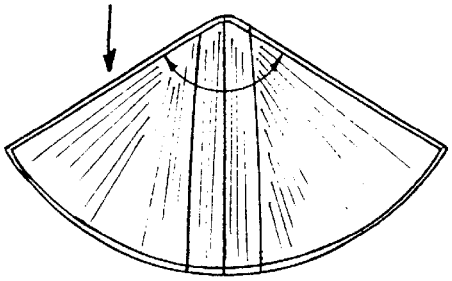
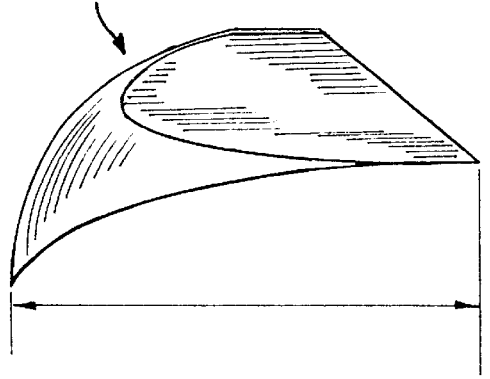

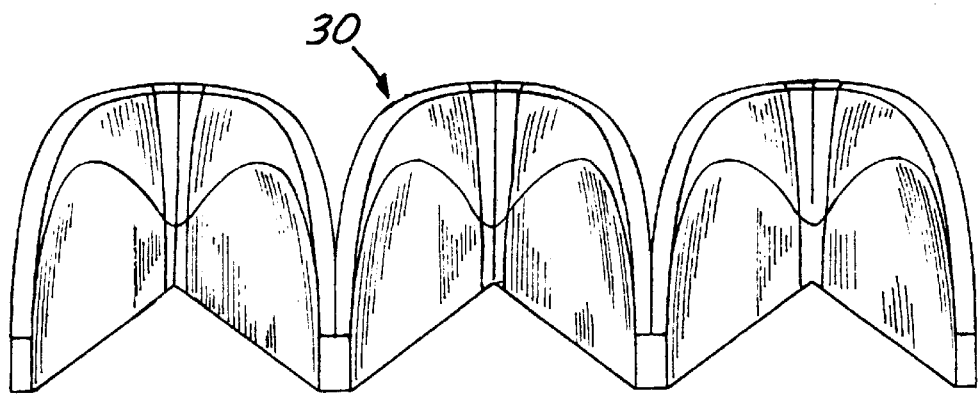
FIG. 6
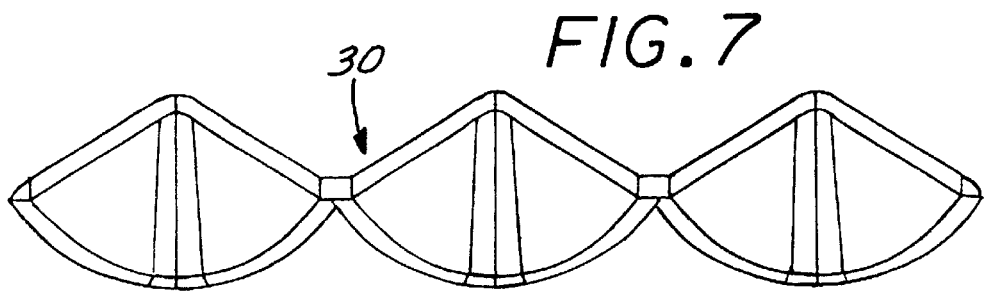
FIG. 7
FIG. 8
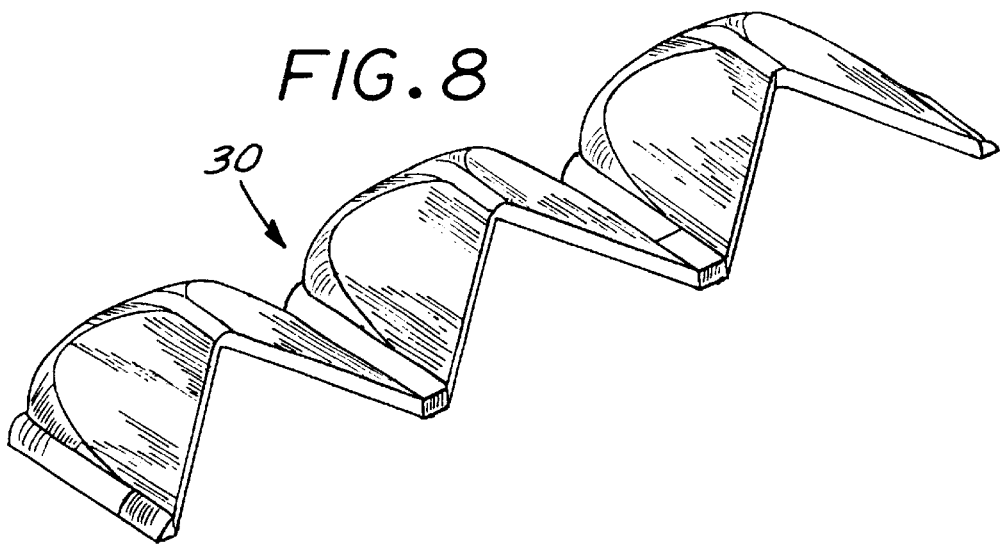

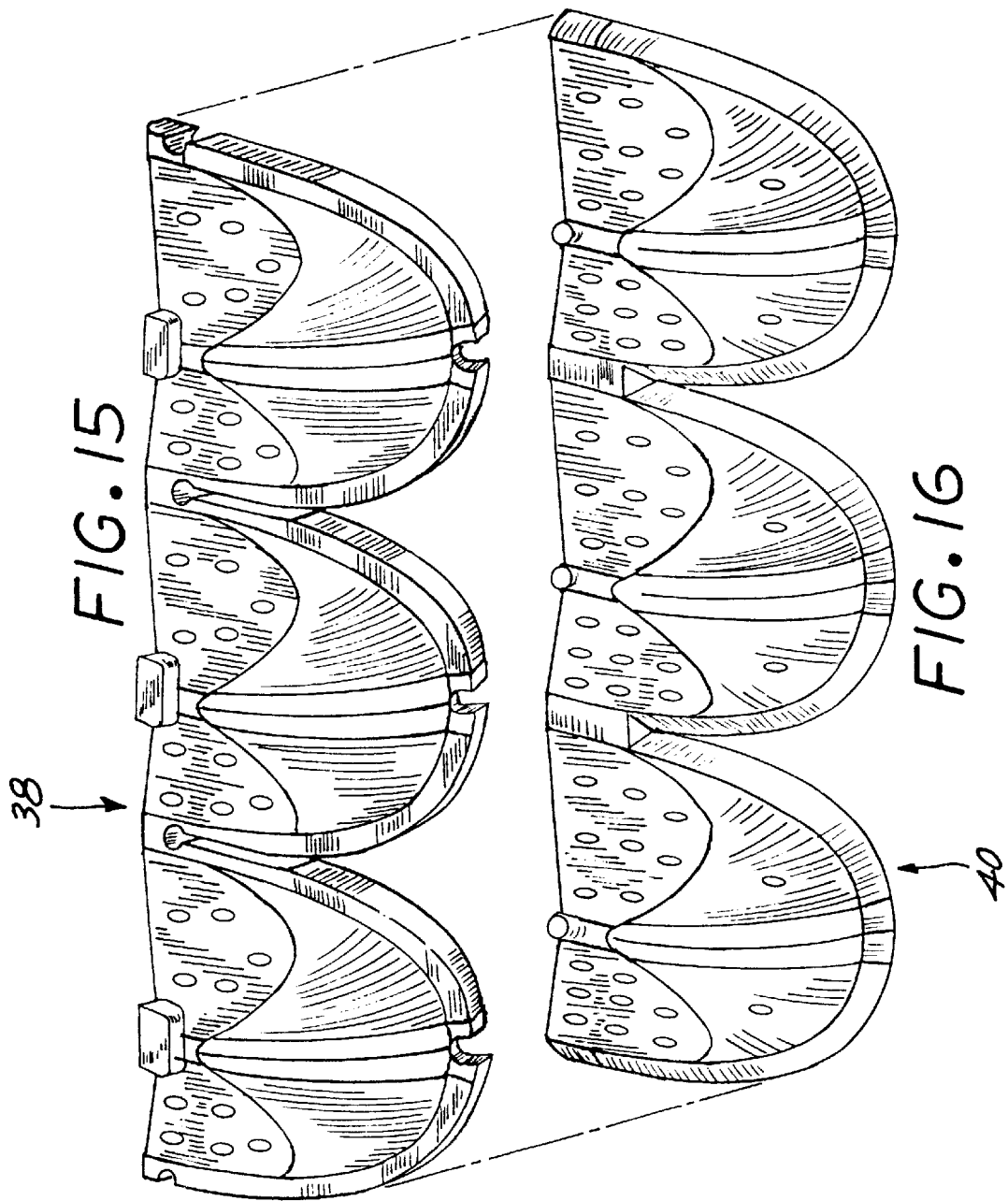

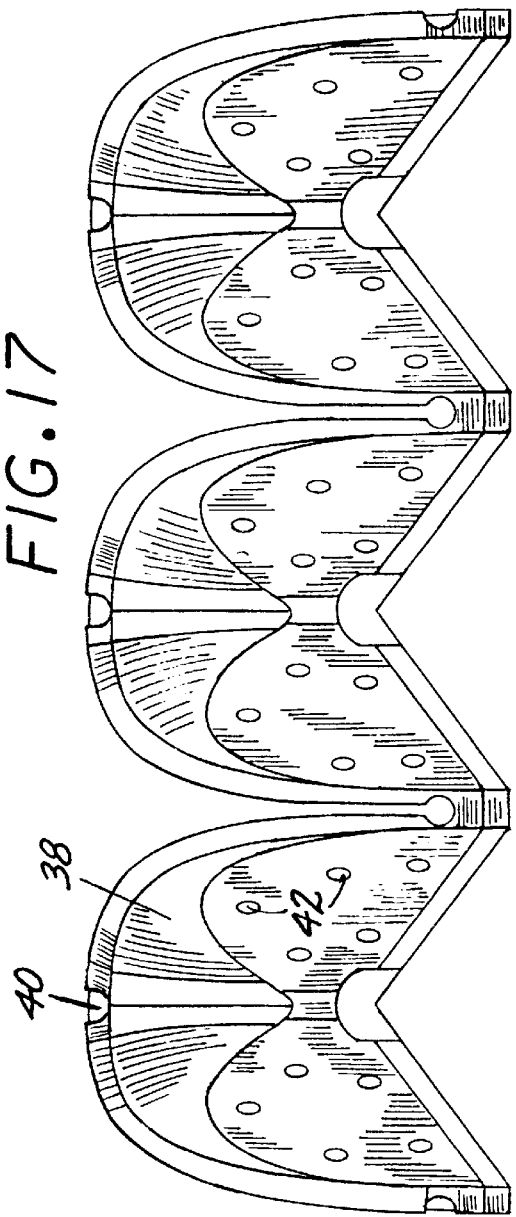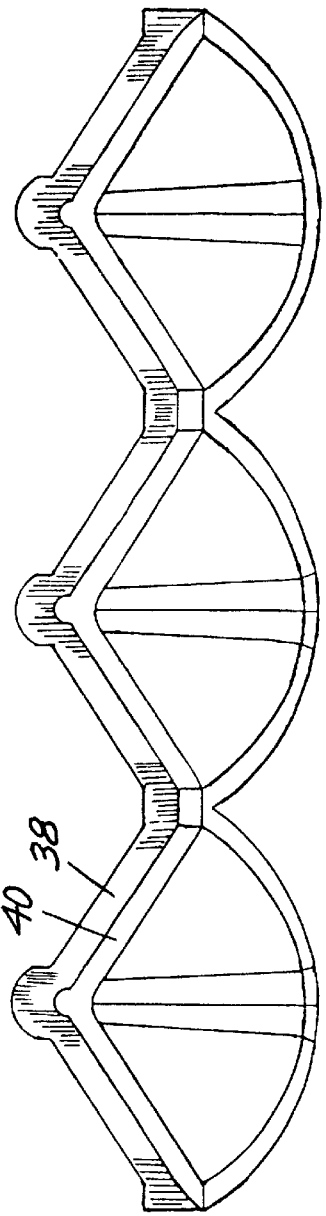

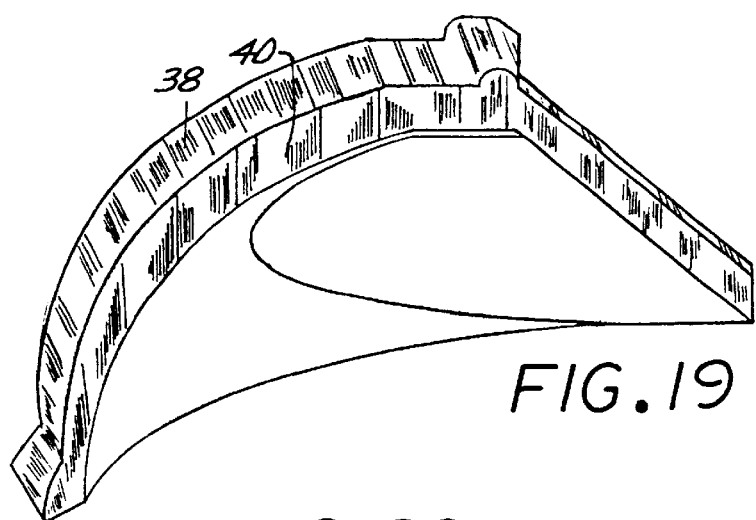
FIG.19
FIG.20
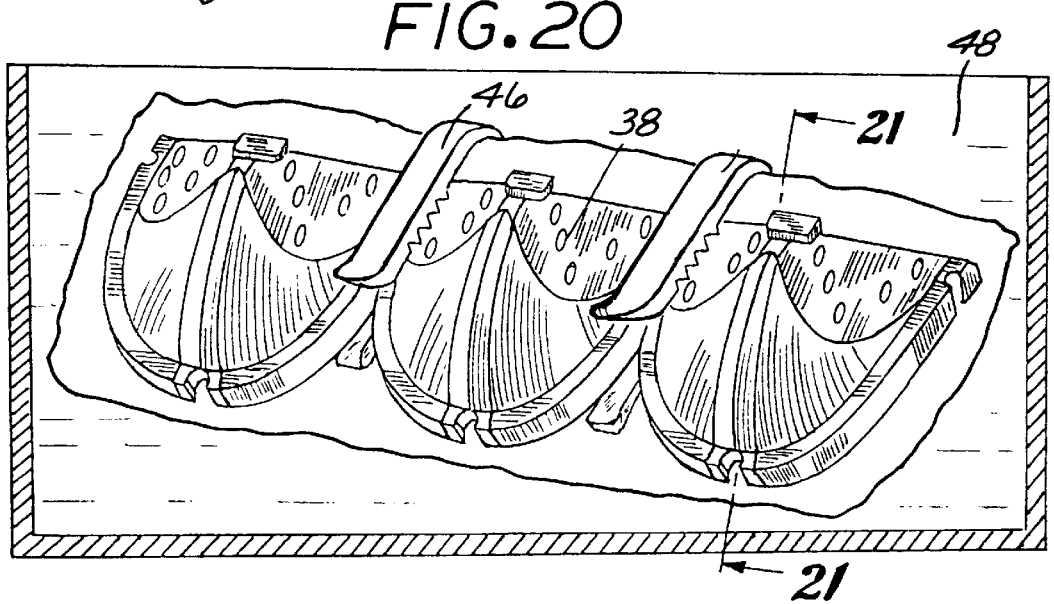
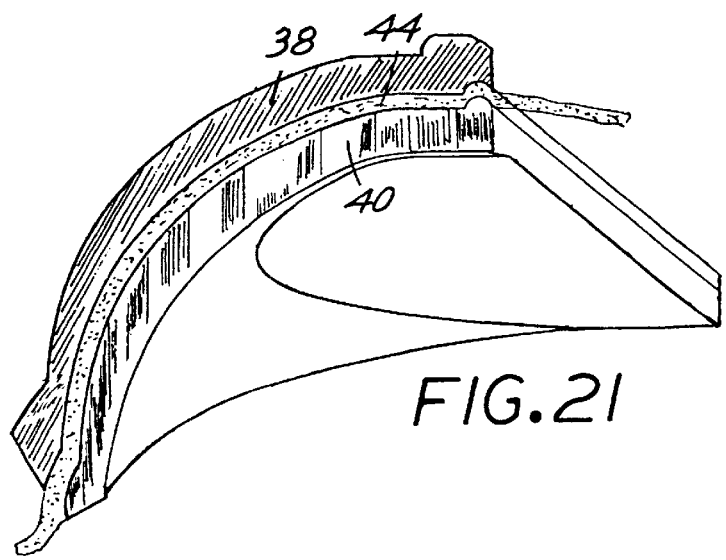
FIG.21

SOLUTION AND METHOD FOR TREATING AUTOLOGOUS TISSUE FOR IMPLANT OPERATION

BACKGROUND OF THE INVENTION

1. Field of the Invention

The present invention is in the field of methodology and materials for performing autologous tissue transplants. More particularly, the present invention is directed to a solution suitable for treating autologous tissue after the tissue has been removed from a mammal, to render the tissue more suitable for handling and molding it into the desired shape and obtain predictable results after implantation in the mammal.

2. Brief Description of the Prior Art

Significant advances have been made in the field of treatment of defective heart valves due to abnormalities during fetal development, or due to infectious or degenerative diseases. These surgical treatments most often require the use of biocompatible materials that can be either synthetic polymers or of biological origin, either from the patient (autologous), an individual of the same species (homologous), or different species (heterologous or xenograft). Defective heart valves are replaced with mechanical valves or tissue valves, such as cadaver or animal aortic valves (bioprosthesis). Because of their more-or-less predictable mechanical wear properties, the mechanical prostheses have been proven suitable for their intended purpose, primarily in younger patients. However, mechanical prostheses have their disadvantages because patients having them require long-term, constant and vigorous anti-coagulant therapy. In older patients however the bioprostheses have been favored mainly because they do not require anti-coagulation therapy, and in older patients they do not tend to undergo calcification as often as they tend to do in younger patients. Cryo-preserved homografts have been used widely in the western world during the recent years. However, these are hard and expensive to obtain, ship and store, and their availability on a world-wide basis appears to be limited.

As is known, heart valve repair or replacement and many other implant operations require soft connective tissue which in preparation for implantation needs to be sized and cut into specific shapes. A substitute for such soft connective tissue of biological origin can be provided by flat sheets of certain synthetic materials. However, it is difficult to find synthetic materials which can match the compliance of the native tissue they are intended to replace, and which do not engender adverse reaction by the recipient of the implant. Autologous tissues, such as pericardium, hold the promise for an ideal soft tissue replacement material in implants, and fresh autologous pericardium has been used in the prior art as a tissue source for repairing a variety of heart lesions, including heart valves. However, results with the use of such fresh untreated autologous tissue were less than satisfactory because tissue contraction distorted the repair, and in case of heart valves, tended to render the leaflets non-functional some time after operation. Generally speaking, the problem with fresh autologous soft connective tissue, such as pericardium, is that such tissues are often too soft and flexible to cut and otherwise handle especially during open heart surgery where an atmosphere of urgency prevails. As an improvement Dr. Duran (one of the inventors of the present invention) developed a procedure in which the autologous tissue that has been freshly obtained from the patient operated on, is treated with 0.5% glutaraldehyde in a mold for 10 minutes. Thereafter, it is cut into the desired shape dictated by the mold and is placed in the patient as new replacement heart valve leaflets. Although this procedure works reasonably well, the disadvantage of tissues treated by glutaraldehyde is that, similarly to xenografts, such tissues may well undergo calcification in long term implants.

The present invention provides an alternative to glutaraldehyde fixation of autologous tissues and yet eliminates the problems caused by contraction of fresh tissue and the difficulty of handling and manipulating soft tissue. Because the invention avoids the above-noted problems by treating the autologous tissue with an aqueous solution of alcohols and other materials, prior art describing solutions and methods for treating biological tissues and specimens are thought to be of interest as background to the present invention. Such prior art can be found in U.S. Pat. Nos. 5,558,875; 5,296,514; 5,276,006; 4,323,358 and 4,329,492. Among the foregoing, the most recently issued U.S. Pat. No. 5,558,875 describes a process of preparing a collagenous prosthesis by soaking tissue in an organic detergent for sufficient time to disrupt the cell membrane and to solubilize the cellular membrane proteins of the collagenous tissue and thereafter extracting and removing the cellular membrane proteins from the collagenous tissue by mechanical washing to obtain the prosthesis and thereafter preserving the prosthesis in alcohol. The process is said to preserve the elasticity of the prosthesis.

The following articles or scientific publications also provide background of interest to the present invention: Chachques et al., Ann. NY Acad Sci. 1988, 529:184; Love et al., J. Heart Valve Dis 1992: 1:232–41; Chauvaud et al., J. Thorac Cardiovasc Surg. 1991, 102:171–8; Duran et al., J. Thorac Cardiovasc Surg. 1995, 11-511–6; Vyavahare et al., 4th Scientific Meeting International Association for Cardiac Biological Implants, Washington D.C., May, 1997; Ritter et al., Plastic & Reconstructive Surgery. 101 (1): 142–6, January, 1998; and Vetter et al., J. Thorac Cardiovasc Surg, 35(1):11–5, February 1987.

SUMMARY OF THE INVENTION

It is an object of the present invention to provide a composition (solution) and method for treating autologous soft tissue so as to render it easier to handle and shape for implantation, while avoiding disadvantages caused by aldehyde treatment of such tissue.

It is another object of the present invention to provide a composition (solution) and method that meets the foregoing objective and which treats the autologous soft tissue during a surgical procedure and while said procedure is in progress.

The foregoing and other objects and advantages are attained by exposing for approximately 2 to 8 minutes a fresh autologous tissue, such as pericardium, to an aqueous solution containing approximately 10 to 70% by volume of a water-miscible non toxic polar solvent, such as ethyl alcohol, approximately 2 to 30% by weight of polyethylene glycol of a molecular weight between approximately 6,000 to 15,000 D, and approximately 0.01 to 1.0% by weight of heparin. The tissue preferably, and most frequently in accordance with the procedure is immersed in the above-described solution while placed in a suitable mold. In case of preparing the tissue for heart valve replacement the mold is configured to provide the appropriate shape and dimension for the replacement heart valve leaflets. The soft tissue implant treated in the foregoing manner temporarily becomes more rigid and easier to handle during surgical procedure than unprepared fresh tissue. However, within approximately the time taken to perform the surgical procedure of implantation the treated tissue regains its original physical properties, including its elasticity.

BRIEF DESCRIPTION OF THE DRAWING FIGURES

FIG. 1 is a schematic perspective view showing the general configuration of one cusp of a negative template of a mold used for shaping an aortic valve replacement from autologous tissue, utilizing the novel solution and method of the present invention.

FIG. 2 is a schematic perspective view showing the general configuration of one cusp of a positive template of the mold used for shaping an aortic valve replacement from autologous tissue, utilizing the novel solution and method of the present invention.

FIG. 3 is a top plan view of the negative cusp of FIG. 1.

FIG. 4 is an end plan view of the negative cusp of FIG. 1.

FIG. 5 is a side plan view of the negative cusp of FIG. 1.

FIG. 6 is a schematic top plan view showing the general configuration of three negative cusps of FIG. 1 assembled to form a negative template used for shaping an aortic valve replacement from autologous tissue, utilizing the novel solution and method of the present invention.

FIG. 7 is a front plan view of the negative template of FIG. 6.

FIG. 8 is a schematic perspective view of the negative template of FIG. 6.

FIG. 15 is a perspective view of the first preferred embodiment of the negative template of FIG. 9.

FIG. 16 is a perspective view of the first preferred embodiment of the positive template of FIG. 12.

FIG. 17 is a top plan view showing the first preferred embodiment of the negative template of FIG. 9 and the first preferred embodiment of the positive template of FIG. 12 assembled to one another.

FIG. 18 is a front plan view showing the first preferred embodiment of the positive template of FIG. 9 and the first preferred embodiment of the negative template of FIG. 12 assembled to one another.

FIG. 19 is a partial cross-sectional view taken on lines 19,19 of FIG. 18.

FIG. 20 is a view showing the assembled mold of FIG. 18 having autologous tissue and immersed in a solution in accordance with the present invention.

FIG. 21 is a partial cross sectional view of the mold with autologous tissue, the cross-section being taken on lines 21,21 of FIG. 20.

DESCRIPTION OF THE PREFERRED EMBODIMENTS

Figure 9:
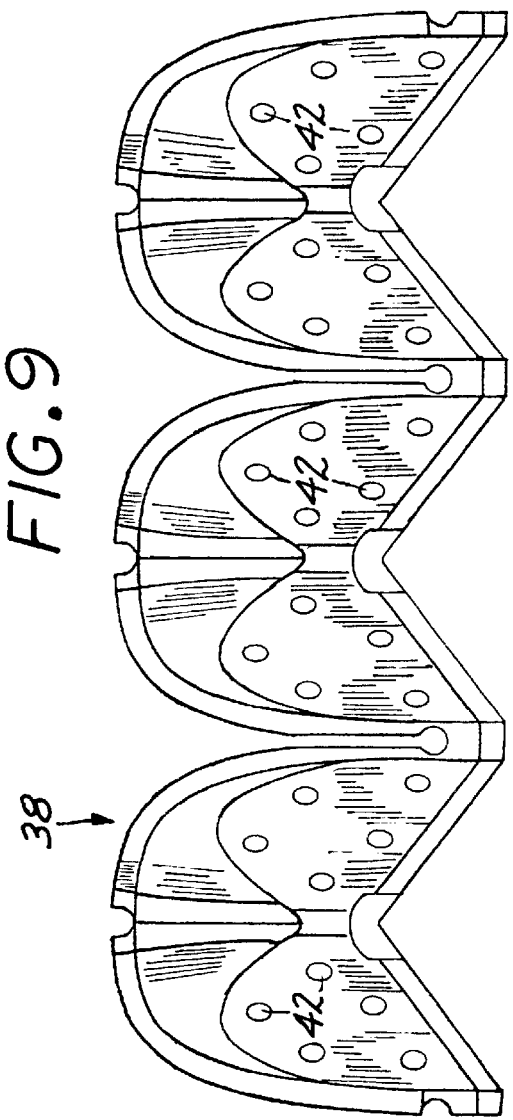
FIG. 9 is a detailed top plan view of a first preferred embodiment of a negative template used for shaping a pericardial valve replacement from autologous tissue, utilizing the novel solution and method of the present invention.
Figure 11:
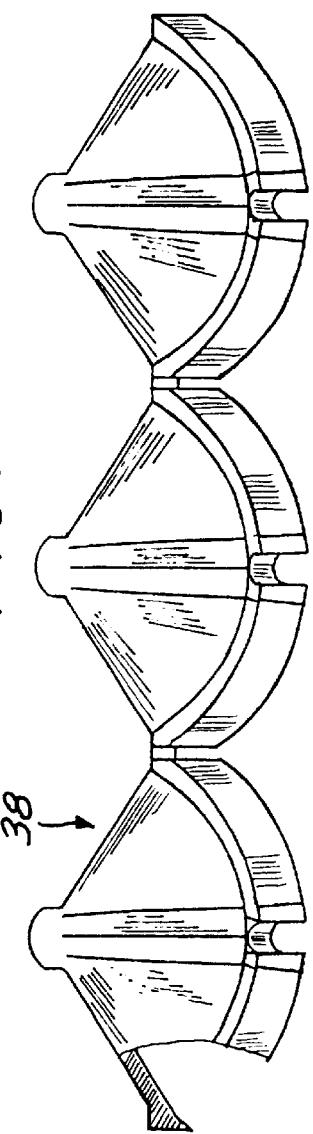
FIG. 11 is a front plan view of the first preferred embodiment of the negative template of FIG. 9, with part of the front material broken away.
Figure 10:
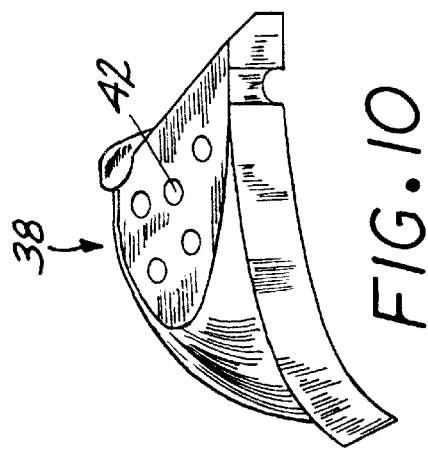
FIG. 10 is an end view of the first preferred embodiment of the negative template of FIG. 9.
Figure 12:
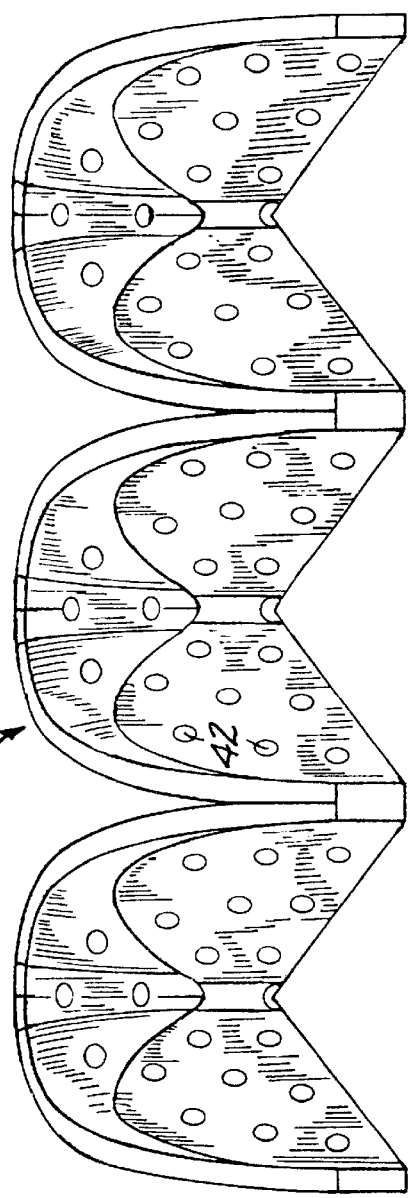
FIG. 12 is a detailed top plan view of a first preferred embodiment of a positive template used for shaping a pericardial valve replacement from autologous tissue, utilizing the novel solution and method of the present invention.
Figure 14:
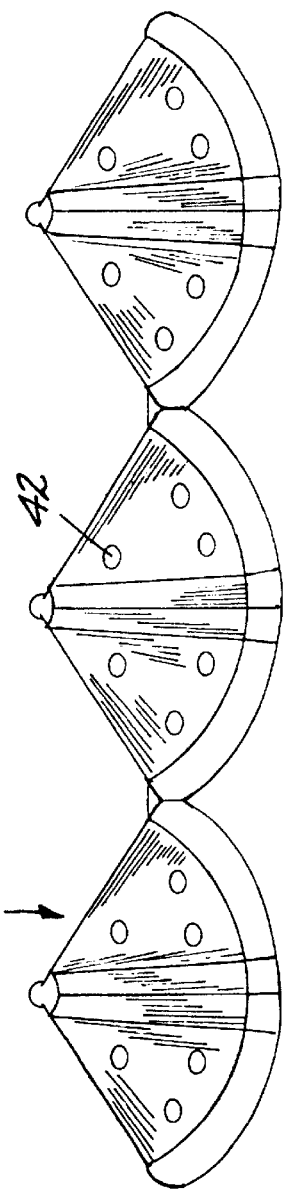
FIG. 14 is a front view of the first preferred embodiment of the positive template of FIG. 12.
Figure 13:
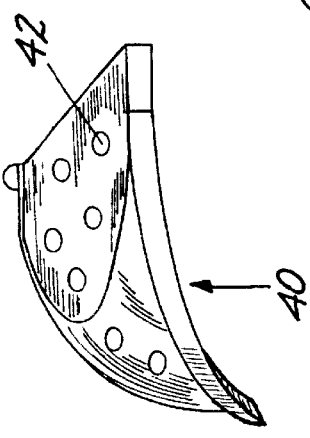
FIG. 13 is an end view of the first preferred embodiment of the positive template of FIG. 12.

The present invention is practiced in conjunction with a surgical procedure wherein a heart valve, aortic, pulmonary, tricuspid or mitral, or other biological membrane is replaced or repaired. Because its most frequent use is in conjunction with replacement of defective membranes in the heart, the present invention is described here primarily as it pertains to replacement of defective heart valves. In accordance with the present invention the operating surgeon excises a membrane-like fresh autologous tissue from the patient and by application of the solution of the present invention changes the physical properties of the fresh autologous tissue to be better suited for trimming, handling, and manipulation during implantation into the patient. Membrane-like tissues which are suitable to be handled and implanted in accordance with the present invention include the peritoneum, pericardium, gut, dennis pleura and tendon. For open heart surgery and replacement of defective heart valves the use of the patient's pericardium is preferred, and therefore the invention is described herein primarily in connection with the use of pericardium as the membrane-like autologous tissue.

In accordance with the invention, the freshly obtained pericardium (or other membrane-like autologous tissue) is treated with an aqueous solution containing approximately 10 to 70% by volume of a water-miscible non-toxic organic solvent, approximately 2 to 30% by weight of polyethylene glycol of a molecular weight between approximately 6,000 to 15,000 D, and approximately 0.01 to 1.0% by weight of heparin, the rest of the solution being water. Examples of suitable water-miscible organic solvents or liquids are lower alkyl, especially $C_1$ to $C_3$ alcohols, such as methanol, ethanol and iso-propanol, and acetone, acetonitrile and methyl ethyl ketone. A more preferred range of the components in the solution in accordance with the present invention is approximately 15 to 60% by volume of the water-miscible organic liquid, 2 to 10% by weight of polyethylene glycol, and 0.1 to 0.7% by weight of heparin.

Preferably the organic solvent is ethyl alcohol, and in the presently most preferred embodiment of the solution there is approximately 50% by volume ethanol, approximately 5% by weight of polyethylene glycol having a molecular weight of approximately 8,000 D, and approximately 0.5% by weight of heparin. The biological membrane is thoroughly exposed to the solution for sufficient time to provide the desired results of rendering the membrane more rigid and therefore easier to trim, suture and otherwise handle. However, usually a time limit is set to this exposure by the fact that the process occurs while the patient is undergoing surgery, usually open heart surgery. It was found in practice that approximately 2 to 8 minutes of exposure of the biological membrane to the solution is sufficient. Nevertheless, under circumstances where the surgical procedure per se does not represent a time-limiting factor, the biological membrane can be kept in the solution for indefinite length of time provided the solution is kept under sterile condition. Treatment by this solution kills the living cells in the membrane although treatment with the solution containing organic solvent at the lower end of the above-described range may only kill cells on the surface of the membrane and merely retards the biological response of cells in the interior. Nevertheless, unlike treatment with glutaraldehyde, treatment with the solution of the present invention does not result in any cross-linking of the membrane materials. The biological membrane or tissue becomes more rigid or stiff during exposure to the solution partly because of the hypertonic, dehydrating nature of the solution.

Hardening or stiffening of the membranes is temporary, however, because after sufficient rinsing with saline or upon equilibration with isotonic biological fluids, such as blood, the biological membranes regain virtually completely their original physical properties, and as a result are well suited for their intended function as replacement of natural membranes, primarily as heart valves.

A preferred manner of practicing the present invention, together with molds that are used for shaping pericardium or other biological membranes to provide aortic and pericardial heart valve replacements are illustrated in the drawing figures. Referring now back to the Brief Description of the Drawing Figures, FIGS. 1 through 8 schematically illustrate the basic geometry of a mold comprising a negative 30 and a positive 32 template for forming an aortic valve replacement in accordance with the present invention. FIGS. 1 through 5 schematically illustrate the basic geometry of the individual negative 34 and positive 36 cusps of the templates 30 and 32 that together form the mold. The templates 30 and 32 are made from thin plastic material, and are configured and dimensioned to provide the aortic heart valve replacement for the individual patient who is being operated on. As it will be readily understood by those skilled in the art of cardiology and related cardiac surgery, primarily echocardiograms of the patient provide the information as to what size heart valve replacement is needed. Edges of the templates 30 and 32 are beveled or rounded in order to facilitate trimming of excess tissue with a surgical knife.

In accordance with one manner of practicing the invention, the pericardium (or other suitable biological membrane) is placed into the mold between the negative and postive templates and treated for approximately 5 minutes with the solution of the invention by immersion in the solution. Thereafter it is very quickly (for less than 5 seconds) rinsed with saline solution containing approximately 250 unit per ml heparin. This step of treating the tissue with heparin solution for a very brief period of time is not necessary for the successful practice of the invention and is therefore optional. In any event, after removal from the mold and having been trated with the solution of the invention the tissue is more rigid than the native untreated pericardium, and is easier to handle. Excess tissue is then removed by trimming with a surgical knife, the tissue in the shape of heart valve leaflets is removed from the mold, and is thereafter surgically implanted. The increased rigidity or stiffness of these replacement leaflets renders the implantation procedure easier to handle. After suturing is completed, the tissue is irrigated with saline solution, whereupon it regains its original physical properties. As noted above, the biological membrane treated in accordance with the present invention regains its original physical properties upon adequate rinsing with saline, or achieving equilibrium with isotonic aqueous fluid, such as blood.

Figure 22:
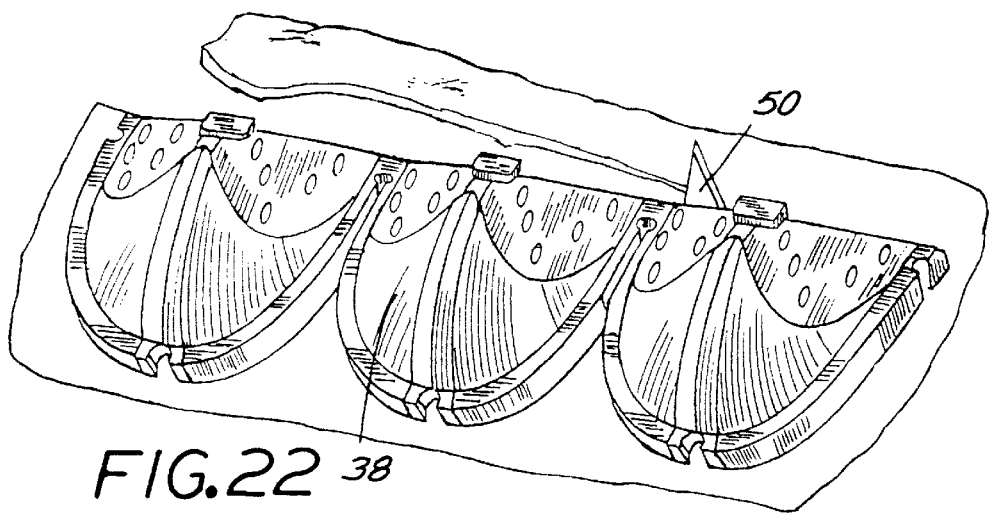
FIG. 22 is a partial schematic view, schematically showing the trimming of excess autologous tissue to form a replacement heart valve, in accordance with the present invention.
Figure 23:
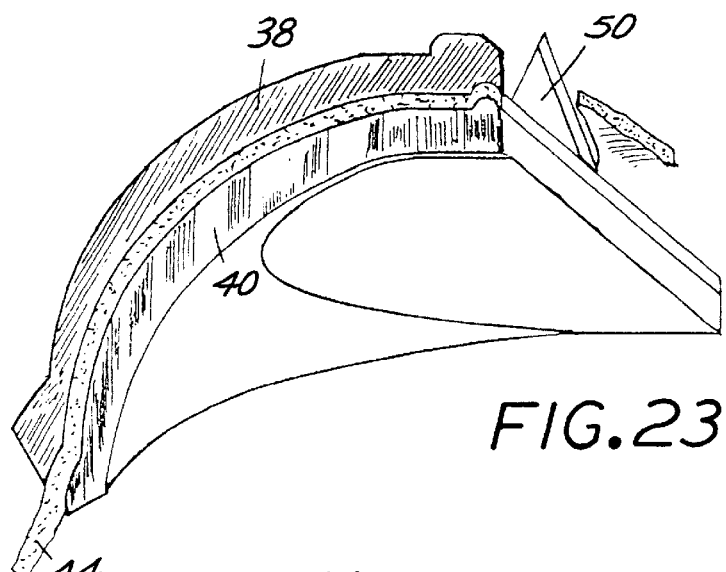
FIG. 23 is a cross-sectional view taken on lines 23,23 of FIG. 22.
Figure 24:
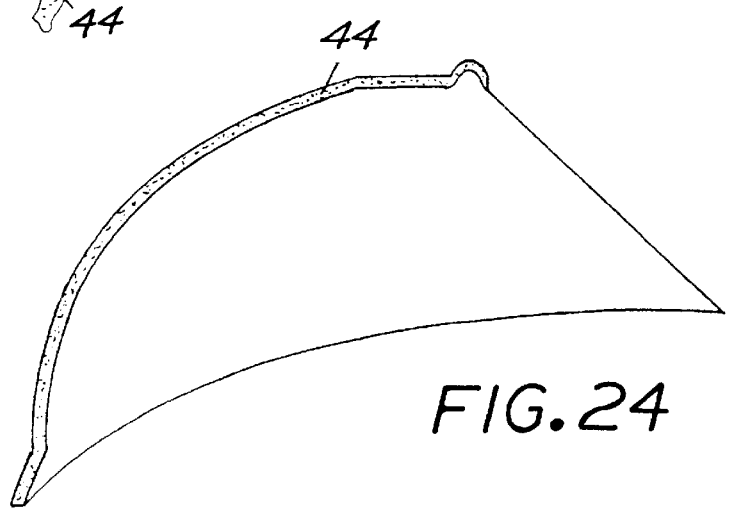
FIG. 24 is a partial cross sectional view of the trimmed autologous tissue.

FIGS. 9 through 24 illustrate in more detail an actual mold comprising a negative template 38 and a positive template 40 adapted for shaping a flat biological membrane, such as pericardium, to form replacement leaflets for a pericardial valve. The two templates 38 and 40 of this mold are made of thin plastic material having beveled edges, and the templates are dimensioned to provide replacement leaflets of appropriate size for the patient who is undergoing the open heart surgery. For use in conjunction with the present invention, the negative 38 and the positive template 40 both are provided with a plurality of apertures 42. When this mold is used in the practice of the present invention, the autologous biological membrane, preferably pericardium excised from the patient who is undergoing open heart surgery, is placed between the templates, 38 and 40, that is into the mold. Accordingly, the pericardium, shown in FIGS. 21 through 24 as 44 is sandwiched between the two templates 38 and 40. The two templates of the mold are held together with suitable plastic clips 46, shown in FIG. 20. The mold including the pericardium 44 is then immersed for approximately 5 minutes in the solution 48 of the invention, as is schematically shown in FIG. 20. During this time the solution 48 percolates through the apertures 42 into the pericardium 44 and renders the pericardium 44 more rigid than in its natural native state. After removal from the solution, the tissue 44 is trimmed with a surgical instrument along the beveled edges of the mold. The surgical instrument is schematically shown in FIG. 22 and bears the reference numeral 50. The resulting replacement heart leaflets (not shown) are then removed from the mold, and may be quickly (less than 5 seconds) rinsed with saline solution containing approximately 250 unit per ml heparin. This optional quick rinsing does not yet decrease the rigidity of the tissue which was the result of treatment with the solution. Surgical implantation of the replacement leaflets is greatly facilitated by its increased rigidity or stiffness. After implantation, the replacement leaflets are irrigated with saline and regain their original physical properties. A substantial advantage of the heart valve replacements obtained in accordance with the present invention is that, unlike replacement valves made of autologous tissues in the prior art, the replacement valves of the invention do not contract or shrink after implantation. Generally speaking, implants of autologous tissues which have been treated in accordance with the present invention are highly resistant or immune to thickening, contraction or fibrin deposition after the implants are placed into the bloodstream of the host. The above described process of exposing the biological membrane to the solution of the invention while the membrane is held in an appropriately configured and dimensioned mold is the presently preferred mode of practicing the invention.

SPECIFIC EXAMPLES

Fresh autologous tissues were dissected from the sheep and placed on molds which were used as templates for cutting the tissues into a shape which appeared as three half-moons joined together at the base of the half-moon. This particular shape was designed for the purpose of aortic or pulmonary heart valve cusp extension operation. Pericardial tissues cut according to this design can be directly implanted into the heart of the individual patient where the tissue is derived from. The tissues in the mold were immersed into a solution containing 50% by volume of alcohol, 5% by weight of polyethylene glycol (MW=8,000)

and 0.5% by weight of heparin for five minutes at room temperature. The tissues in the mold were removed from the solution and after the removal of excess liquid outside the tissues, the tissues were rinsed in saline containing 250 unit/ml of heparin for less than 5 seconds.

Tissues treated with the solution mentioned above appeared to be slightly translucent and natural in color. Unlike the fresh untreated tissues, the treated tissues were stiffer so that it was relatively easy to lift the tissues without the tissues folding onto themselves. The treated tissues were easily spread on a flat or curved surface with different markings for cutting the tissues. Since the cut tissues maintained their shape, they were easily implanted as replacement leaflets of heart valves. Yet, once the suturing of the tissues was completed and a small amount of saline was irrigated onto the implanted tissues, the tissues became soft quickly. Within the time required to close the open heart, the physical properties of the tissues became indistinguishable from the fresh untreated tissues. Therefore the resulting implants function perfectly as repaired heart valves.

Human fibroblasts and umbilical cord vein endothelial cells were cultured on the treated tissues after there were rinsed in saline containing 250 unit/ml of heparin to study their biocompatibility. Round discs of the tissues were cut to fit the bottom of the wells of a 24 well culture plate. Tygon$^R$ flexible rings were placed on top of the tissues to ensure a good seal at the edge of the tissues. Cells were seeded on the tissues in normal culture media for one week. At the end of the incubation period, tissues were recovered and processed for histology. Both human umbilical cord vein endothelial cells and human skin fibroblasts attached and proliferated on the treated tissues as evidence that after rinsing in saline the treated tissue is not cytotoxic and biocompatible for host cells to attach and proliferate. The attachment and proliferation of endothelial cells and other connective tissue cells on cardiac implants is potentially important for the long term survival of the implant.

Integrity of the collagen fibers in the treated tissues was examined by melting temperature measurements. Tissues were heated in phosphate buffered saline from 37° C. until they shrunk. The shrinkage temperature of the treated tissues after they were rinsed in saline was 64±1° C. which is identical to untreated fresh tissue indicating that the collagen fibers remained intact throughout the treatment and saline-rinse process.

Efficacy of the treated tissues as useful cardiovascular implants was tested by implanting the treated autologous tissues in the descending aorta of sheep in different configurations. A piece of pericardium was dissected and divided into three pieces with different shapes, namely a trapezoid, a strip made into a conduit and a square. These pieces of tissues were implanted serially in the descending aorta of sheep. The trapezoid shaped tissue was implanted upstream as a patch on the aortic wall, next to it downstream the short conduit was implanted and further downstream a square shaped tissue was placed as a semi-free flap across the lumen inside the aorta with two edges of the square attached to opposite side of the inner wall of the aorta. When fresh autologous tissues were implanted under the same condition, the semi-free flap in the aorta lumen became fibrotic and contracted within 30 days. However the patch and the conduit upstream, that was implanted in accordance with the present invention did not show the same reaction. There was also evidence of thrombus formation and fibrin deposition on the surfaces of the fresh implants. When the treated implants (not rinsed in saline) were implanted in sheep in the same manner all implants remained intact after 30 days without any evidence of fibrotic reaction and tissue contraction. Thrombus and fibrin deposition were minimal or absent on these implants.

In still other further examples fresh bovine pericardial tissues were treated using the solution of the invention. The treated tissues were cut and trimmed to sizes and shapes suitable for valve repairs. The treated and trimmed tissues were sutured in the aortic roots of isolated human and porcine hearts. The whole hearts were than mounted on a pulse duplicator to examine the competency of the repair valve. The treated tissues were very flexible and the reconstructed valves functioned normally as competent aortic valves.

What is claimed is:

1. An aqueous composition adapted for treating autologous biological tissue for modifying its tissue reactivity and for rendering the tissue temporarily more rigid than in its natural state, the composition comprising:
   approximately 10 to 70% by volume of a water miscible non-toxic organic solvent selected from the group consisting of an alcohol having 1 to 3 carbons, acetone, acetonitrile and methyl ethyl ketone;
   approximately 2 to 30% by weight of polyethylene glycol having a molecular weight in the range of approximately 6,000 to 15,000 D;
   approximately 0.01 to 1.0% by weight of heparin, and
   the balance of the composition substantially consisting of water.

2. The liquid composition of claim 1 wherein the water miscible organic solvent is ethyl alcohol.

3. The liquid composition of claim 2 that contains approximately 15 to 60% ethyl alcohol.

4. The liquid composition of claim 3 that contains approximately 50% ethyl alcohol.

5. The liquid composition of claim 1 that contains approximately 2 to 10% polyethylene glycol.

6. The liquid composition of claim 5 that contains approximately 5% polyethylene glycol.

7. The liquid composition of claim 5 wherein the polyethylene glycol has a molecular weight of approximately 8,000 D.

8. The liquid composition of claim 1 that contains approximately 0.1 to 0.7% heparin.

9. The liquid composition of claim 8 that contains approximately 0.5% heparin.

10. An aqueous liquid composition adapted for treating autologous biological tissue for modifying its tissue reactivity and for rendering the tissue temporarily more rigid than in its natural state, the composition comprising:
    approximately 15 to 60% by volume of ethyl alcohol;
    approximately 2 to 10% by weight of polyethylene glycol of a molecular weight of approximately 8,000 D;
    approximately 0.1 to 0.7% by weight of heparine, and
    the balance of the composition substantially consisting of water.

11. The liquid composition of claim 10 comprising approximately 50% ethyl alcohol, approximately 5% polyethylene glycol and approximately 0.5% heparine.

12. A method for modifying the tissue reactivity of an autologous tissue freshly obtained from a host mammal and for rendering the tissue temporarily more rigid than in its native state, the method comprising:
    exposing said autologous tissue to an aqueous composition, comprising:
    approximately 10 to 70% by volume of a water miscible non-toxic organic solvent selected from the group consisting of an alcohol having 1 to 3 carbons, acetone, acetonitrile and methyl ethyl ketone;

approximately 2 to 30% by weight of polyethylene glycol having a molecular weight in the range of approximately 6,000 to 15,000 D;

approximately 0.01 to 1.0% by weight of heparin, and the balance of the composition substantially consisting of water.

13. The method of claim 12 where in the liquid composition the water miscible organic solvent is ethyl alcohol.

14. The method of claim 13 where the liquid composition contains approximately 15 to 60% ethyl alcohol.

15. The method of claim 13 where the liquid composition contains approximately 2 to 10% polyethylene glycol.

16. The method of claim 13 where the liquid composition contains approximately 0.1 to 0.7% heparin.

17. The method of claim 13 where the liquid composition contains approximately 50% ethyl alcohol, approximately 5% polyethylene glycol of a molecular weight of approximately 8,000 D and approximately 0.5% heparin.

18. The method of claim 12 where the autologous tissue freshly obtained from a host mammal comprises a biological membrane.

19. The method of claim 12 where the autologous tissue is selected from a group consisting of peritoneum, pericardium, pleura and tendon.

20. The method of claim 12 wherein the step of exposing the autologous tissue to the liquid composition is by immersing the tissue in the liquid composition.

21. The method of claim 20 further comprising the step of placing the autologous tissue in a mold.

22. The method of claim 21 wherein the autologous tissue is placed in the mold before the tissue is exposed to the liquid composition, and wherein the tissue is exposed to the liquid composition while it is held in said mold, thereby forming said tissue into a predetermined configuration.

23. The method of claim 22 further comprising the step of trimming excess autologous tissue by cutting while said tissue is still in the mold and after it has been exposed to said liquid composition for at least approximately 2 to 8 minutes.

24. The method of claim 23 further comprising the step of implanting the trimmed tissue into the host.

25. The method of claim 24 further comprising the step of irrigating the implanted tissue with isotonic saline solution thereby causing the physical properties of the tissue to return to their substantially native state.

* * * * *